United States Patent [19]

Kennedy et al.

[11] 3,997,570

[45] Dec. 14, 1976

[54] ALKENYL HALOLACTONE ESTERS

[75] Inventors: Brian R. Kennedy, San Rafael; Warren Lowe, El Cerrito, both of Calif.

[73] Assignee: Chevron Research Company, San Francisco, Calif.

[22] Filed: May 19, 1975

[21] Appl. No.: 579,125

Related U.S. Application Data

[60] Continuation-in-part of Ser. No. 335,284, Feb. 23, 1973, abandoned, which is a division of Ser. No. 169,544, Aug. 5, 1971, Pat. No. 3,755,173.

[52] U.S. Cl. .............................. 260/343.6; 536/63; 536/110; 536/119
[51] Int. Cl.$^2$ ...................................... C07D 307/32
[58] Field of Search ............. 260/343.6; 200/210 R

[56] References Cited

UNITED STATES PATENTS

| | | | |
|---|---|---|---|
| 3,155,685 | 11/1964 | Prill et al. | 260/343.6 |
| 3,155,686 | 11/1964 | Prill et al. | 260/343.6 |
| 3,248,187 | 4/1966 | Bell | 44/63 |
| 3,267,062 | 8/1966 | Prill et al. | 260/343.6 |
| 3,813,416 | 5/1974 | Heiba et al. | 260/343.6 |

*Primary Examiner*—Henry R. Jiles
*Assistant Examiner*—CMS Jaisle
*Attorney, Agent, or Firm*—G. F. Magdeburger; C. J. Tonkin; L. L. Priest

[57] ABSTRACT

Alkenyl halolactone esters of monools and polyols are described. These materials are useful as lubricating oil detergency and/or dispersancy additives.

15 Claims, No Drawings

ALKENYL HALOLACTONE ESTERS

CROSS-REFERENCE TO RELATED APPLICATIONS

This application is a continuation-in-part of U.S. application Ser. No. 335,284, filed Feb. 23, 1973 now abandoned, which is a Divisional of U.S. application Ser. No. 169,544, filed Aug. 5, 1971, which has issued into U.S. Pat. No. 3,755,173.

BACKGROUND OF THE INVENTION

1. Field of the Invention

This invention concerns novel alkenyl halolactone esters of monools and polyols and lubricating oil compositions containing those esters as metal-free ("ashless") detergent or dispersant additives.

It has long been recognized that lubricating oils designed for use in internal combustion engines should possess significant detergency or dispersancy characteristics. This is necessary so that the deposits of varnish and sludge which would otherwise accumulate on pistons, cylinder walls, crankcases and other surfaces within the engine will be minimized. Accumulation of such deposits adversely affects the efficient operation of the engine. This reduced efficiency in turn results in excessive pollutant emissions by the engine, reduced power and reduced engine life.

Early lubricating oil detergent and dispersant additives were metal-containing compounds such as metal sulfonates. These left an undesirable residue or "ash" in the engine. More recently, there have been developed a number of so-called ashless additives which contain no metal. These are exemplified by the widely used alkenyl succinimides. There is a constant need in the lubricant industry for ashless detergents and dispersants which combine the properties of high detergency or dispersancy, low cost, good oil solubility and ease of preparation.

2. Description of the Prior Art

Amide derivatives of alkyl substituted lactone esters are described in U.S. Pat No. 3,200,075.

SUMMARY

We have now discovered an effective ashless detergent/dispersant additive which consists of the reaction product of (1) a monool or polyol and (2) an alkenyl chlorolactone or bromolactone alkyl ester or acid which has been prepared by the reaction alkenyl succinic anhydride, chlorine or bromine, and a low molecular weight alkanol or water. The invention also encompasses the lubricant compositions comprising an oil of lubricating viscosity and the described additive.

DETAILED DESCRIPTION OF THE INVENTION

The compositions of this invention are novel metal-free (ashless) lubricating oil detergency/dispersancy additives and lubricants containing those additives. These lubricants provide excellent detergency and/or dispersancy in both diesel and gasoline internal combustion engines. In diesel engine tests in which the engine is operated under extremely severe conditions, these lubricants have proved to be quite effective in maintaining a low level of deposits in the engines. The additive imparts to the lubricant a number of desirable properties, as illustrated in the examples below.

Preparation of the Compositions

The additive composition of this invention is the reaction product of a monool or polyol and an alkenyl chlorolactone or bromolactone alkyl ester or acid. The ester or acid is prepared by reacting an alkenyl succinic anhydride, chlorine or bromine, and a low molecular weight alkanol or water, respectively.

The alkenyl succinic anhydride from which the alkenyl chlorolactone or bromolactone alkyl ester or acid is prepared is of the following formula:

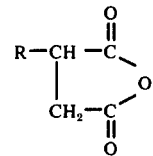

wherein R is an alkenyl group most conveniently obtained by polymerizing an olefin mixture of olefins containing from about 2 to 5 carbon atoms. THe molecular weight of the resulting polymer will generally be in the range of about 400 to 3000 and more usually in the range of about 700 to 1400. Useful olefins are illustrated by ethylene, propylene, 1-butene, 2-butene, isobutene 1-pentene and mixtures thereof, preferably isobutene. The methods of polymerizing such olefins to polymers of the designated molecular weight are well known in the art and do not require exemplification here. (See, for example, U.S. Pat. Nos. 3,024,195 and 3,018,250.)

The alkenyl succinic anhydride is converted to the alkenyl chloro- or bromolactone alkyl ester or acid by reaction in solution with chlorine or bromine and, for the ester, a low molecular weight alkanol, or, for the acid, water. The low molecular weight alkanols are those conataining 1–3 carbon atoms and no functional groups other than a single hydroxy group. The alkanols thus include methanol, ethanol, 1-propanol, and 2-propanol. Of these methanol and ethanol (particularly methanol) are preferred.

The halogens which may be used to produce the alkenyl halolactone ester or acid are chlorine and bromine. The remaining halogens, fluorine and iodine, generally do not give satisfactory reaction products. The chlorine is usually present as chlorine gas, which is bubbled through the reaction mixture. Bromine is present as liquid in the reaction mixture. Alternatively, one may use a compound which will donate chlorine or bromine (such as N-bromosuccinimide) but which will otherwise not participate to any significant degree in the reaction of the anhydride, alkanol and chlorine or bromine. The residue of such a compound should also be readily separable from the reaction mixture.

The reaction of anhydride, chlorine or bromine, and alkanol or water is ordinarily carried out at ambient temperature and pressure for a period of 0.1–12, preferably 0.5–6, hours. The anhydride and alkanol or water are mixed in an inert solvent (such as mineral oil) and the halogen is added to or bubbled through the mixture. Alternatively, but less preferably, the materials may be reacted neat or in an excess of alkanol or water. Equimolar amounts of the reactants may be used. Usually, however, at least a molar excess of methanol and excess halogen are used to insure maximum reaction. Heating of the mixture is not necessary for the reaction is slightly exothermic. If desired, cooling means may be provided to maintain the reaction mixture at a temperature at or slightly above ambient temperature. Following reaction the solvent and excess reactants are removed and the product recovered.

The alkenyl halolactone alkyl ester or acid product will generally contain about 1–8 weight percent chlorine or bromine. The infrared spectrum of the product will show distinctive peaks at about 1775–1780 cm$^{-1}$ (lactone) and about 1740 cm$^{-1}$ (ester) or about 1700 cm$^{-1}$ (acid).

The alkenyl halolactone alkyl ester or acid and the mono- or polyol are reacted with heating to a temperature in the range of 170°–190° C. for a period of 1–24 hours. The reaction is conducted in the presence of a small amount of hydroxide anion and under a nitrogen or other inert gas atmosphere. Usually approximately equimolar amounts of reactants are used, although a small excess of mono- or polyol may be used if desired. The esterification or transesterification reaction may be caused to proceed to completion by removal during the reaction of the low molecular weight alkanol or water produced. The product may be recovered by conventional means, including separation of unreacted mono- or polyol, which may be recovered.

The monools or polyols which are useful in the abovedescribed esterification or transesterification reaction may be selected from any of the following: (1) aliphatic or alicyclic monohydric and polyhydric compounds, either saturated or unsaturated, (2) aromatic monohydric or polyhydric compounds, and (3) mixtures thereof. Preferred are the polyhydric compounds having at least three hydroxyl groups. Also preferred are those monohydric or polyhydric compounds which are unsubstituted, i.e., contain only carbon, hydrogen and alcoholic oxygen atoms.

The aliphatic or alicyclic alcohols from which the esters may be derived preferably contain up to about 40 aliphatic carbon atoms. They may be monohydric alcohols such as methanol, ethanol isooctanol, dodecanol, cyclohexanol, cyclopentanol, behenyl alcohol, hexatriacontanol, neopentyl alcohol, isobutyl alcohol, benzyl alcohol, β-phenylethyl alcohol, 2-methylcyclohexanol, monomethyl ether of ethylene glycol, monobutyl ether of ethylene glycol, monopropyl ether of diethylene glycol, monododecyl ether of triethylene glycol, monooleate of ethylene glycol, monostearate of diethylene glycol, sec.-pentyl alcohol, tert.-butyl alcohol, and dioleate of glycerol.

The polyhydric alcohols preferably contain from 2 to about 10 hydroxyl groups. They are illustrated by ethylene glycol, diethylene glycol, triethylene glycol, tetraethylene glycol, dipropylene glycol, tripropylene glycol, dibutylene glycol, tributylene glycol, and other alkylene glycols in which the alkylene group contains from 2 to about 8 carbon atoms. Other useful polyhydric alcohols include glycerol, monooleate of glycerol, monostearate of glycerol, monomethyl ether of glycerol, pentaertythritol, 9,10-dihydroxy stearic acid, methyl ester of 9,10-dihydroxy stearic acid 1,2-butanediol, 2,3-hexanediol, 2,4-hexanediol, pinacol, erythritol, arabitol, sorbitol, mannitol, 1,2-cyclohexanediol, and xylene glycol. Carbohydrates such as sugars, starches, celluloses, etc., likewise may yield the esters of this invention. The carbohydrates may be exemplified by glucose, fructose, sucrose, rhamnose, mannose, glyceraldehyde, and galactose.

A preferred class of polyols consists of ethylene glycol, diethylene glycol, triethylene glycol, tetraethylene glycol, dipropylene glycol, tripropylene glycol, dibutylene glycol, pentaerythritol, sorbitol, mannitol, and arabitol.

An especially preferred class of polyhydric alcohols are those having at least three hydroxyl groups, such as pentaerythritol, sorbitol, mannitol, and arabitol. Solubility of some polyhydric alcohols may be increased by esterifying some of the hydroxyl groups with a monocarboxylic acid having from about 8 to about 30 carbon atoms such as octanoic acid, oleic acid, stearic acid, linoleic acid, dodecanoic acid, or tall oil acid. Examples of such partially esterified polyhydric alcohols are the monooleate of sorbitol, distearate of sorbitol, monooleate of glycerol, monostearate of glycerol, and didodecanoate of erythritol.

The esters of this invention may also be derived from unsaturated alcohols such as allyl alcohol, cinnamyl alcohol, propargyl alcohol, 1-cyclohexene-3-ol, and oleyl alcohol.

The aromatic hydroxy compounds from which the esters of this invention may be derived are illustrated by the following specific examples: phenol, β-naphthol, α-naphthol, cresol, resorcinol, catechol, p,p′-dihydroxybiphenyl, 2-chlorophenol, 2,4-dibutylphenol, propene tetramer-substituted phenol, didodecylphenol, 4,4′-methylene-bis-phenol, α-decyl-β-naphthol, polyisobutene(molecular weight of 300–2000)-substituted phenol, the condensation product of heptylphenol with 0.5 mole of formaldehyde, the condensation product of octylphenol with acetone, di(hydroxyphenyl)oxide, and 4-cyclohexylphenol. Phenol and alkylated phenols having up to three alkyl substituents are preferred. Each of the alkyl substituents may contain 100 or more carbon atoms.

The alkenyl halolactone mono- or polyol ester reaction product will contain 0.5–5 weight percent chlorine or bromine, and its infrared spectrum will contain peaks at about 1740 cm$^{-1}$ (ester), 1780 cm$^{-1}$ (lactone), and 3450 cm$^{-1}$ (hydroxyl).

The Lubricant Compositions

The lubricant compositions of this invention are prepared by blending the ester reaction product as an additive into an oil of lubricating viscosity. Suitable oils are derived from either natural or synthetic sources and generally have viscosities of from about 35 to 50,000 Saybolt Universal Seconds (SUS) at 100° F. Among natural hydrocarbonaceous oils are paraffin-base, naphthenic-base, asphaltic-base and mixed-base oils. Illustrative of synthetic oils are hydrocarbon oils such as polymers of various olefins, generally of from 2–8 carbon atoms, and alkylated aromatic hydrocarbons; and nonhydrocarbon oils such as polyalkylene oxide, aromatic ethers, carboxylate esters, phosphate esters and silicon esters. The preferred media are the hydrocarbonaceous media, both natural and synthetic. The above oils may be used individually or together whenever miscible or made so by the use of mutual solvents.

When the detergents and/or dispersants of this invention are compounded with lubricating oils for use in an engine, they will be present in a concentration of at least about 0.01 weight percent and usually not more than 20 weight percent, more usually in the range of about 0.5–15, and preferably 1–10, weight percent. Often higher concentrations are used in diesel engine lubricants than are used in gasoline engine lubricants. The compounds can also be prepared as concentrates due to their excellent compatibility with oils. As concentrates, the compounds of this invention will generally range from about 10–70 weight percent, more usually from about 20–50 weight percent of the total composition.

The lubricants may contain other known additives such as extreme pressure and antiwear agents, antioxidants, pour point depressants, oiliness agents, rust inhibitors, colorants, foam suppressants, etc. Usually, the total amount of these additives will range from about 0.1–15 weight percent, more usually from about 0.5–5 weight percent. The individual additives may vary from about 0.01–5 weight percent of the composition.

In a preferred aspect, the lubricant compositions of this invention will include (in addition to the ester reaction product detergent/dispersant) 1–50 mM./kg. of a dihydrocarbyl phosphorodithioate, wherein the hydrocarbyl groups are from about 4–36 carbon atoms. Usually the hydrocarbyl groups will be alkyl or alkaryl groups. The remaining valence of the phosphorodithioate will usually be satisfied by zinc, but polyalkyleneoxy or a third hydrocarbyl group may also be used. ("Hydrocarbyl" designates an organic radical composed solely of carbon and hydrogen, and which may be aliphatic, alicyclic, or aromatic.)

Exemplification of the Compositions

EXAMPLE 1

Preparation of Alkenyl Chlorolactone Methyl Ester

To a 3-liter flask equipped with a stirrer were charged 1300 g. of oil-free polyisobutyl succinic anhydride (in which the isobutyl portion of the molecule had a molecular weight of approximately 950), 100 cc. of methanol and 800 cc. of benzene solvent. These reagents were thoroughly mixed and then chlorine gas was bubbled through the mixture while stirring for 3–½ hours. During this period, the temperature of the reaction mixture ranged between 77° F. and 110° F. Thereafter nitrogen was bubbled through the chlorinated mixture for 10 hours and the product was recovered by stripping under vacuum. 1397 g. of product were obtained, with a chlorine content 4.5 weight percent. The infrared spectrum included peaks at 1740 cm$^{-1}$ and 1775 cm$^{-1}$.

Although the actual reaction product is a mixture of compounds, the structures of which are not all known with certainty, it is believed that among the reactions occurring is the following:

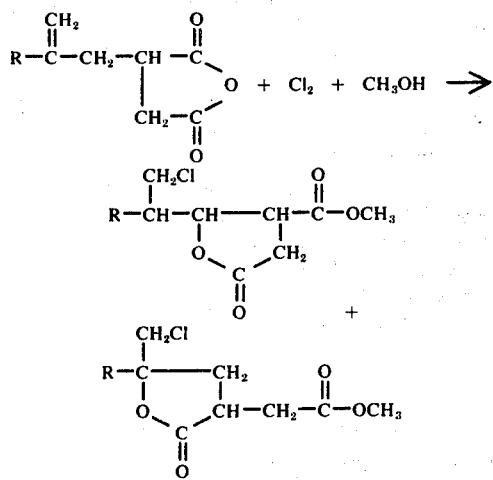

(This reaction scheme, and those elsewhere in this specification, is meant only to indicate the general nature of the reactions occurring. None is to be considered definitive or limiting as to structures or compounds actually obtained.)

EXAMPLE 2

Reaction of Pentaerythritol and Alkenyl Chlorolactone Methyl Ester 1300 g. of the reaction product of Example 1 were mixed with 159 g. of pentaerythritol and 0.8 g. of sodium hydroxide. The reagents were stirred under a nitrogen atomosphere for 12 hours at approximately 180° C. The product was dissolved in mixed hexanes, allowed to settle and then filtered through Celite 545. The product was recovered by boiling off the hexanes and stripping under vacuum. 1242 g. of the chlorolactone pentaerythritol ester reaction product were recovered. This product contained approximately 2.6 weight percent of chlorine. The infrared spectrum included peaks at 1740, 1775, and 3440 cm$^{-1}$. The product had a total base number (ASTM D-664) of 32.5 (average of two runs).

As in Example 1, the reaction product will contain a variety of compounds, the structures of which are not known with certainty. However, it is believed that among the reactions occurring are:

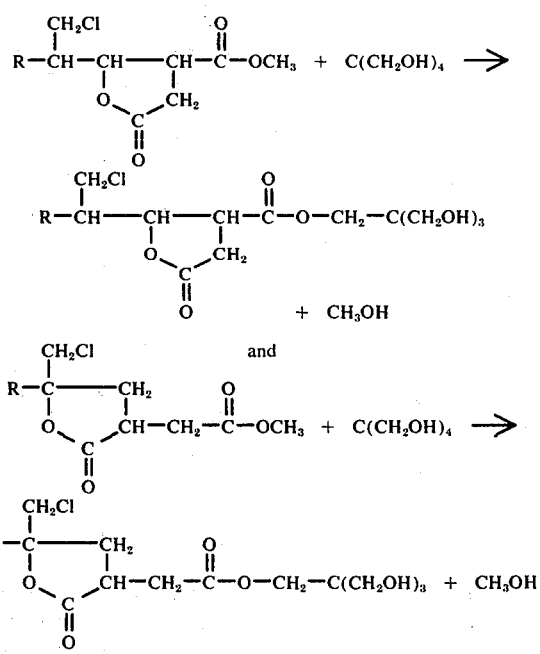

For simplicity, only the reaction of one of the hydroxyl groups on the pentaerythritol has been shown. Obviously, there will be occurring reactions with other hydroxyl groups so that some polyesters may be formed.

EXAMPLE 3

Preparation of Alkenyl Chlorolactone Acid

To a 1-liter flask equipped with a stirrer and heating mantle were charged 325 g. of oil-free polyisobutenyl succinic anhydride of the type described in Example 1, 13 cc. of water, and 200 cc. of benzene solvent. Chlorine gas was bubbled through the mixture for about one hour. During this hour, the temperature ranged between 78° F. and 120° F. Thereafter nitrogen gas was bubbled through the chlorinated mixture for two hours and the product was recovered by stripping under vacuum. 339 g. of product were obtained, with a chlorine content of 3.9 weight percent.

As in the above examples, the exact composition of the reaction product mixture is not known with certainty. However, it is believed that among the reactions occurring is the following:

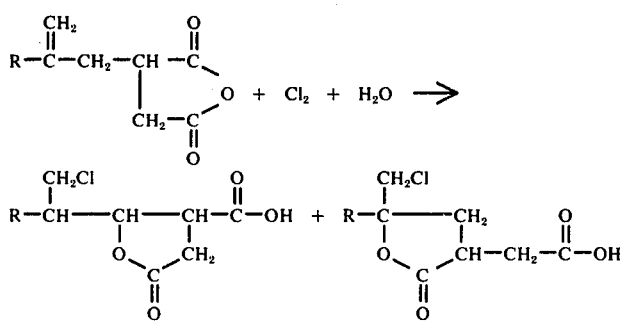

EXAMPLE 4

Reaction of Pentaerythritol and Alkenyl Chlorolactone Acid 167 g. of the reaction product of Example 3 were mixed with 20 g. of pentaerythritol and 0.2 g. of NaOH. The reaction was conducted as in Example 2, to yield a product having a chlorine content of 2.27 weight percent. The infrared spectrum included peaks centered at about 1730 $cm^{-1}$, 1780 $cm^{-1}$, and 3460 $cm^{-1}$. The product had a total base number (ASTM D-664) of 76.5 (average of two runs). The typical reactions believed to be occurring are esterifications with water as a product analogous to the transesterifications illustrated in Example 2.

Lubricant Composition Performace Data

In order to illustrate the utility of the chlorolactone pentaerythritol esters as lubricant additives, a number of bench and engine tests were run using lubricants containing these esters. The results of each of these tests are described below.

EXAMPLE 5:

Ford 6 Piston Varnish Test

The Ford 6 test is designed to indicate the ability of a lubricant to keep varnish deposits from forming on engine pistons. The test uses a Ford 6-cylinder in line engine of 240 in³ displacement with a 4.00 in. bore and a 3.18 in. stroke. The engine is operated with a Ford economy carburetor with a manually adjustable jet in place of the power valve. Fuel and air feed rates are measured, and the air/fuel ratio controlled to 15.0 ± 0.5 by adjusting the jet during Cycle 3 running (see below). The engine is run on a 3-cycle test series. The conditions of each cycle are described on Table I following.

TABLE I

| Cycle | Throttle | RPM | Jacket Temp., °F. | Oil Temp., °F. | Duration, mins. |
|---|---|---|---|---|---|
| 1 | Idle | 750 | 115 | 120 | 45 |
| 2 | Wide Open | 2500 | 125 | 175 | 135 |

TABLE I-continued

| Cycle | Throttle | RPM | Jacket Temp., °F. | Oil Temp., °F. | Duration, mins. |
|---|---|---|---|---|---|
| 3 | Wide Open | 2500 | 170 | 205 | 60 |

The entire series requires 4 hours and is ordinarily run four times without cooling the engine for a 16-hour total test run. At the end of the run, the engine is disassembled and the piston skirts rated for varnish using the CRC Rating Manual No. 1. If desired, a more severe test can be obtained by repeating the 16-hour test one or more additional times. In the examples reported below in Table II, the lubricant compositions used were composed of a hydrocarbon lubricating oil prepared by blending a 200 neutral oil, a 350 neutral oil and a 150 bright stock, and as additives, 50 mM./kg. of an overbased calcium sulfonate, 15 mM./kg. of a zinc dialkyldithiophosphate and the indicated weight percent of the test additive. The designation "PBCLPE" is an abbreviation for the polyisobutenylchlorolactone pentaerythritol ester of Example 2. The designation "Succinimide A" refers to a commercial polyisobutenyl succinimide produced by reacting a polyisobutenyl succinic anhydride (PIBSA) with tetraethylene pentamine (TEPA). The polyisobutenyl portion of the molecule has a molecular weight of approximately 950 and the mole ratio of TEPA/PIBSA is 0.87. The designation "Ester A" refers to a commercial ester prepared by reacting pentaerythritol with a polyisobutenyl succinic anhydride in which the polyisobutenyl portion has a molecular weight of approximately 950–1000.

TABLE II

| Dispersant | Con., Wt., % | Average Piston Varnish Rating[1] | | |
|---|---|---|---|---|
| | | 16 hrs. | 32 hrs. | 48 hrs. |
| PBCLPE | 3 | 7.7 | 7.0 | — |
| Succinimide A | 3 | 9.6 | 6.9 | — |
| PBCLPE | 8 | 8.1 | 7.8 | 6.8 |
| Ester A | 8 | 8.8 | 7.7 | 6.9 |

[1]Scale: 0–10; 10 represents the cleanest piston.

These data clearly indicate that the esters of this invention are good antivarnish additives and that lubricants containing these esters are comparable in performance to lubricants containing commercial additives in their performance in automobile gasoline engines.

EXAMPLE 6:

180 BMEP Caterpillar Diesel Engine Test

The purpose of this test was to illustrate the performance of the lubricants of this invention in diesel engines. This test utilizes a single-cylinder Caterpillar supercharged diesel engine having a 5 ⅛ bore by 6 ½ stroke. The engine is operated at 180 psi BMEP, a fuel input of 7460 BTU/minute, an intake air pressure of 70 inches of mercury and a power output of 55 BHP. Other operating conditions are the same as those used in the well-known Caterpillar 1-G test. The test formulation was composed of a hydrocarbon lubricating oil prepared by blending a 250 neutral oil and a 150 bright stock, 100 mM./kg. of an overbased sulfurized calcium alkyl phenate, 2.5 mM./kg. of an overbased calcium sulfonate, 20 mM./kg. of a zinc dialkaryldithiophosphate and 6 percent of the test additive. The designation "Succinimide B" refers to a commercial succinimide similar to Succinimide A above, but prepared by reaction with triethylene tetramnine (TETA) instead of TEPA; the TETA/PIBSA mole ratio is 0.5. The test engine was run for 120 hours, dismantled, and the piston inspected for groove and land deposits. Each groove is rated on a scale of 0–100, with 0 being a clean groove and 100 being a groove completely filled with deposits. Each land is rated on a scale of 0–800, with 0 being a clean land and 800 being a completely dirty land.

TABLE III

| Dispersant | Piston Ratings | |
|---|---|---|
| | Grooves | Lands |
| PBCLPE | 58-8.4-0.5-0.5 | 220-25-20 |
| Succinimide B | 74-6.4-0.5-0.5 | 230-20-55 |

These data clearly indicate that the lubricants of this invention have very good performance in diesel engine and compare favorably with commercial lubricant formulations.

EXAMPLE 7:

Neutralization Rate Test

This is a bench test designed to correlate with the well-known Sequence IIB Automobile Engine Rust Test. This test has been found to give an accurate prediction of the performance of a given additive in the Sequence IIB test. In this test a 100 ml. solution of 0.01 N aqueous HCl is placed in a Beckman "Expandomatic" pH meter. 50 ml. of the test oil are layered into mixture is plotted as a function of time. The test results are reported as the number of minutes elapsed from the beginning of mixing until the curve of pH-versus-time shows a point of inflection; the more quickly this point of inflection occurs, the more rapidly the acid has been neutralized by the lubricant composition. The better oils, therefore, give the lowest test numbers. In the test reported below in Table IV, the test formulations were composed of a 100 neutral oil, 25 mM./kg. of the over-based calcium sulfonate of Example 6, 40 mM./kg. of the over-based sulfurized calcium alkyl phenate of Example 6, 15 mM./kg. of the zinc dialkaryldithiophosphate of Example 6, and 8 percent of the test additive.

TABLE IV

| Dispersant | Time to Point of Inspection, mins. |
|---|---|
| PBCLPE | 14.6 |
| Succinimide A | ~35[a] |

TABLE IV-continued

| Dispersant | Time to Point of Inspection, mins. |
|---|---|
| Ester A | 14.8[b] |

[a]average of several runs
[b]average of two runs is apparent from these data that lubricants containing the ester additives of this invention are equal in performance to lubricants containing commercial esters. Further, they are far superior in performance to lubricants containing commercial succinimides.

EXAMPLE 8:

L-38 Strip Corrosion Test

The test was designed to evaluate a lubricant with respect to stability of resistance to oxidation, copper-lead bearing corrosion, and deposition of varnish and/or sludge on engine parts. The test is described in an article by R. W. Jack, Lubrication, 25, 4, 37 (1970) on page 40. The formulations used in the examples in Table V below all were composed of a hydrocarbon 480 neutral oil and 6 weight percent of the test additive. The data are reported as the milligrams of copper or lead lost from the test bearings; the less corrosive loss, the better the lubricant.

TABLE V

| Dispersant | Copper Loss, mg. | | Lead Loss, mg. |
|---|---|---|---|
| | Before KCN | After KCN | |
| PBCLPE | 5 | 8 | 51 |
| Succinimide A | 11 | 13 | 161 |
| Succinimide B | 10 | 12 | 106 |
| Ester A | 17 | 21 | 100 |

It is apparent from these data that the lubricants containing the esters of this invention are far superior to lubricants containing the commercial succinimides or esters in their ability to minimize corrosion.

The above data and examples are intended to be illustratie only. Those skilled in the art will be immediately aware of other embodiments within the scope and spirit of this invention.

We claim:

1. The composition comprising the reaction product of
A. a monool or polyol or mixtures thereof wherein the monool is an unsubstituted $C_1$–$C_{40}$ aliphatic or $C_6$–$C_{40}$ alicyclic alcohol or phenol optionally alkylated with one or two alkyl groups of from one to one hundred carbon atoms and the polyol is selected from ethylene glycol, poly ($C_{2-8}$ alkylene) glycol, glycerol, monooleate of glycerol, monosterate of glycerol, monomethyl ether of glycerol, pentaerythritol, 9,10-dihydroxy stearic acid, methyl ester of 9,10-dihydroxy stearic acid, 1,2-butanediol, 2,3-hexanediol, 2,4-hexanediol, pinacol, erythritol, arabitol, sorbitol, mannitol, 1,2-cyclohexan diol, xylene glycol, glucose, fructose, sucrose, rhamnose, mannose, glyceraldehyde, and galactose and
B. an alkenyl halolactone alkyl ester or acid; said ester being the reaction product of
1. alkenyl succinic anhydride in which the alkenyl group has a molecular weight in the range of 400–3000, 2. halogen selected from chlorine and bromine, and
3. $C_1-C_3$ alkanol;

and said acid being the reaction product of
1. alkenyl succinic anhydride in which the alkenyl group has a molecular weight in the range of 400-14 3000
2. halogen selected from chlorine and bromine, and
3. water.

2. The composition of claim 1 comprising the reaction product of said polyol and said alkenyl halolactone alkyl ester.

3. The composition of claim 2 wherein said polyol is ethylene glycol, diethylene glycol, triethylene glycol, tetraethylene glycol, tripropylene glycol, dibutylene glycol, pentaerythritol, sorbitol, mannitol, or arabitol.

4. The composition of claim 3 wherein said polyol is an unsubstituted polyol containing at least three hydroxyl groups, 5. The composition of claim 4 wherein said polyol is pentaerythritol.

6. The composition of claim 2 wherein said alkenyl group has a molecular weight in the range of from 700 to 1400.

7. The composition of claim 2 wherein said halogen is chlorine.

8. The composition of claim 2 wherein said $C_1-C_3$ alkanol is ethanol or methanol.

9. The composition of claim 8 wherein said $C_1-C_3$ alkanol is methanol.

10. The composition of claim 1 comprising the reaction product of said polyol and said alkenyl halolactone acid.

11. The composition of claim 10 wherein said polyol is ethylene, glycol, diethylene glycol, triethylene glycol, tetraethylene glycol, tripropylene glycol, dibutylene glycol, pentaerythritol, sorbitol, mannitol, or arabitol.

12. The composition of claim 11 wherein said polyol is an unsubstituted polyol containing at least three hydroxy groups.

13. The composition of claim 12 wherein said polyol is pentaerythritol.

14. The composition of claim 10 wherein said alkenyl group has a molecular weight range of from 700 to 1400.

15. The composition of claim 10 wherein said halogen is chlorine.

* * * * *

UNITED STATES PATENT AND TRADEMARK OFFICE
CERTIFICATE OF CORRECTION

PATENT NO. : 3,997,570
DATED : December 14, 1976
INVENTOR(S) : Brian R. Kennedy and Warren Lowe It is certified that error appears in the above-identified patent and that said Letters Patent are hereby corrected as shown below:

Column 1, line 50, "reaction alkenyl" should read --reaction of alkenyl--

Column 2, line 20, "olefin mixture of" should read --olefin or mixture of--

Column 5, line 42, "content 4.5" should read --content of 4.5--

Column 9, line 2, "5-1/8 bore by 6-1/2" should read --5-1/8" bore by 6-1/2"--

Column 9, lines 48 and 49, "50 ml. of the test oil are layered into mixture is plotted as a function of time." should read --50 ml. of the test oil are layered into the aqueous phase and then mixed. During mixing the ph of the mixture is plotted as a function of time.--

Column 10, line 17, "The test was" should read --This test is--

Column 10, line 43, "illustratie" should read --illustrative--

Column 11, line 3, "3) C-$C_3$" should read --3) $C_1$-$C_3$--

Column 11, line 7, "400-14 3000" should read --400-3000--.

Signed and Sealed this

Twenty-second Day of March 1977

[SEAL]

Attest:

RUTH C. MASON
Attesting Officer

C. MARSHALL DANN
Commissioner of Patents and Trademarks